US006268223B1

(12) United States Patent
Cornell-Bell et al.

(10) Patent No.: US 6,268,223 B1
(45) Date of Patent: Jul. 31, 2001

(54) ASSAY FOR DETECTING DAMAGE TO THE CENTRAL NERVOUS SYSTEM

(75) Inventors: Ann H. Cornell-Bell, Westbrook, CT (US); Kathleen S. Madden, Bethesda, MD (US); Leslie A. Riblet, Killingworth, CT (US)

(73) Assignee: Viatech Imagin, LLC, Ivoryton, CT (US)

( * ) Notice: Subject to any disclaimer, the term of this patent is extended or adjusted under 35 U.S.C. 154(b) by 0 days.

(21) Appl. No.: 09/384,356

(22) Filed: Aug. 27, 1999

(51) Int. Cl.[7] .................................................. G01N 33/553
(52) U.S. Cl. ........................ 436/526; 435/7.1; 435/7.94; 435/975; 436/518; 436/523; 436/533; 436/538; 436/546; 436/63; 530/380
(58) Field of Search ..................................... 435/7.1, 7.94, 435/975; 436/518, 523, 526, 533, 538, 546, 63; 530/380

(56) References Cited

U.S. PATENT DOCUMENTS 5,223,398 * 6/1993 Kortright et al. .

OTHER PUBLICATIONS

Harris et al. Journal of Clinical Immunology. vol. 15, No. 5, 1995.*
Krupinski et al, Acta Neurobiol. Exp. 58:13–21, 1998.*
Adams et al., Guidelines for the Management of Patients with Acute Ischemic Stroke, *Stroke*, 25(9): 1901–1914, Sep. 1994.
Bazan, Effect of Ischemia and Electroconvulsive Shock on the Free Fatty Acid Pool in the Brain., *Biochim. Biophys. Acta*, 218: 1–10, 1970.

Buttner et al., S–100 Protein: Serum Marker of Focal Brain Damage After Ischemic Territorial MCA Infarction, *Stroke*, 28: 1961–1965, 1997.
Conn's Current Therapy, R. E. Rakel, ed., W. B. Saunders Co. (1993), pp. 840–851.
Dippel et al., We Need Stronger Predictors of Major Vascular Events in Patients With a Recent Transient Ischemic Attack or Nondisabling Stroke, *Stroke*, 28: 774–776, 1997.
Feinberg et al., Guidelines for the Management of Transient Aschemic Attacks, *Stroke*, 25(6): 1320–1335, Jun. 1994.
Madden et al., Glutamate, Arachidonic Acid, and Calcium Regulation in Cultured Hippocampal Astrocytes: Involvement in Ischemic?, in *Cellular and Molecular Mechanisms of Ischemia Brain Damage. Advances in Neurology*, Siesjo and Wieloch, eds., Lippincott–Raven (Philadelphia 1996), 71: 53–60.

(List continued on next page.)

*Primary Examiner*—Christopher L. Chin
*Assistant Examiner*—Terri Ivory-McCaa
(74) *Attorney, Agent, or Firm*—Leon R. Yankwich; Thomas R. Berka

(57) ABSTRACT

A method is disclosed for the rapid diagnosis of disorders characterized by an ischemic event, such as stroke, transient ischemic attack, head trauma, myocardial infarction or other insults resulting in interrupted cranial blood flow. The method involves detection of the presence of the gamma isoform of protein kinase C (PKCg) in peripheral blood, which signals damage to central nervous system tissue and at least transient breakdown of the blood brain barrier. The assay may be performed, e.g., by emergency medical personnel, in a time frame that allows treatment of the patient before permanent damage to the central nervous system occurs.

20 Claims, 5 Drawing Sheets

OTHER PUBLICATIONS

Missler et al., S–100 Protein and Neuron–Specific Enolase Concentrations in Blood as Indicators of Infarction Volumne and Prognosis in Acute Ischemic Stroke, *Stroke*, 28: 1956–1960, 1997.

Shashoua et al., Proteins of the Brain Extracellular Fluid: Evidence for Release of S–100 Protein, *J. Neurochem.*, 42(6): 1536–1541, 1984.

Wieloch et al., "Intracellular Signal Transduction in the Postischemic Brian," In *Cellular and Molecular Mechanisms in Ischemic Brain Damage: Advances in Neurology.*, Siesjo and Wieloch, eds., Lippincott–Raven (Philadelphia 1996), 71: 371–388.

Wolfe, Eicosanoids: Prostaglandins, Thromboxanes, Leukotrienes and Other Derivatives of Carbon–20 Unsaturated Fatty Acids, *J. Neurochem.*, 38: 1–14, 1982.

Zhao et al., Hyperthermia complicates middle cerebral artery occlusion induced by an intraluminal filament, *Brain Res.*, 649: 253–259, 1994a.

Zhao et al., Delayed treatment with the spin trap alpha–phenyl–N–tert–butyl nitrone (PBN) reduces infarct size following transient middle cerebral artery occlusion in rats, *Acta Physiol. Scand.*, 152: 349–350, 1994b.

\* cited by examiner

ASSAY FOR DETECTING DAMAGE TO THE CENTRAL NERVOUS SYSTEM

FIELD OF THE INVENTION

The present invention discloses a method for the rapid and accurate detection of damage to the central nervous system (CNS) caused by an ischemic event such as stroke or head trauma. The method focuses on detecting the release of the gamma isoform of protein kinase c (PKCg) into the bloodstream, e.g., as a result of the breakdown of the blood-brain barrier. The current invention provides a diagnostic method and a diagnostic kit that is useful for the early diagnosis and treatment of an ischemic event. Such methods and kits may be advantageously used, e.g., by emergency medical personnel, to obtain an early indication of an ischemic event within a time period following the event where permanent CNS damage may be avoided. The methods and kits may also be used to monitor patient progress and recovery following an ischemic event.

BACKGROUND OF THE INVENTION

Brain ischemia resulting from stroke, head trauma or other events that interfere with blood flow to the brain is a leading cause of death and disability in industrialized nations. Stroke, for example, affects 0. 1–0.2% of the North American and European population. Approximately 500,000 people in the United States have a new or recurrent stroke each year, with a significant number resulting in death. An estimated 3,000,000 people in the United States have survived a stroke, however many of these survivors are considered to be at risk for recurrent episodes.

There are no specific neuroprotective drugs on the market to treat ischemic stroke, and consequently this condition represents a major clinical problem with 25–35% fatality for acute strokes within the first three weeks. Of the survivors, 25–50% will be totally dependent on family or institutional care for the rest of their lives.

One major impediment to the establishment of effective therapies for acute CNS injury has been the lack of definitive diagnostic procedures to permit proper and rigorous clinical trial design. Present diagnostic procedures are usually based on a sudden onset of neurologic signs such as hemiparesis, aphasia, hemianopia altered consciousness or gait disturbances.

The initial evaluation of a suspected stroke patient is time-consuming and usually occurs in the hospital after permanent neuronal damage has already occurred. Although the mechanisms involved in stroke are not fully understood, it has been proposed that the pathology arises from an initial infarct, wherein perfusion pressure and blood flow to CNS tissues are reduced by intracellular and microvascular edema, followed by progressive compression and reduced perfusion in areas adjacent to the infarct. As this process evolves, a series of biochemical events takes place as cell damage progresses. These biochemical events, indicative of cell damage and cell death, may include oxidation of membrane components, free radical formation, altered fatty acid metabolism, activation of the gamma isoform of protein kinase C (PKCg), calcium entry into the cell, and disruption of the blood brain barrier.

If permanent brain damage from ischemic injury is to be avoided, appropriate treatment must be administered within two hours of the suspected insult. However, at the present time, definitive diagnostic procedures for these conditions are inaccurate, expensive, and not readily available to physicians or emergency medical personnel such that accurate diagnosis of stroke or other ischemic injury can be determined or measured within this important two-hour window. This absence of effective diagnostic procedures has also contributed to the lack of new therapies for the treatment or prevention of neuronal damage from stroke or other ischemic events.

Assay techniques have been suggested for a number of potential marker proteins associated with stroke, including neuron-specific enolase (NSE), myelin basic protein, glial fibrillary acidic protein, and S-100 protein (Missler et al., 1997). In most cases these substances are measured in cerebrospinal fluid (CSF), which is obtained by invasive and difficult procedures. Given the short diagnostic window for avoiding permanent injury, it is imperative that diagnostic methods be developed that can be performed using more easily obtainable samples, ideally peripheral blood samples. Even though NSE and S-100 are measurable in blood, peak levels are not found until approximately two days following infarction, which makes them impractical indicators of stroke, even though NSE and S-100 protein do correlate with infarct volume (Missler et al., 1997). Also, none of these markers are specific indicators of general brain damage, and S-100 has been shown to be a normal component of plasma (Shashoua et al., 1984).

As mentioned previously, the initial evaluation of a suspected stroke patient is time consuming and usually occurs after permanent brain damage has occurred. Therefore, it would be advantageous to develop an assay to rapidly quantitate a protein that is uniquely expressed at the early onset of stroke, and that appears in easily obtainable and rapidly assayed biological samples such as peripheral blood.

SUMMARY OF THE INVENTION

The present invention is based on the discovery that a particular isoform of protein kinase C, namely the gamma isoform (abbreviated PKCγ or PKCg herein), appears in the peripheral blood very quickly after an ischemic event in the CNS.

The present invention describes a procedure for the rapid and accurate diagnosis of CNS and especially brain ischemia resulting from stroke, transient ischemia attacks ("TIAs"), head trauma, myocardial infarction, or other events resulting in interrupted spinal or cranial blood flow. The procedure can be easily performed by ambulance or emergency room personnel and can be performed with a venous blood sample and an assay kit as described herein.

The present invention provides an assay for the rapid detection of PKCg, a protein expressed only as a result of the type of cell damage that is characteristic of stroke, transient ischemic attacks ("TIAs"), head trauma, myocardial infarction, or other events or "insults" resulting in interrupted blood flow to structures of the CNS. Other events that might lead to such interrupted blood flow to the CNS include medical interventions, such as surgical procedures, surgical or physical errors, anesthesia, and therapeutic or pharmaceutical interventions.

According to the present invention, a peripheral blood sample is drawn from the affected individual then analyzed for the presence of PKCg. Preferably, a venous blood sample is contacted with an anti-PKCg antibody specific for a PKCg epitope under conditions suitable for the formation of an anti-PKCg antibody/PKCg binding complex. Detection of the presence of PKCg in the blood sample, e.g., by detection of the antibody/PKCg complex, indicates a CNS ischemic injury.

In addition to determining whether or not damage to the central nervous system has occurred, i.e., by the presence or absence of PKCg in the blood sample, the present invention also provides for quantitation of the PKCg to determine the severity of the ischemic event. The quantity of PKCg in the original peripheral blood sample is directly correlated to the amount or severity of central nervous system damage.

Where immunosorbant methods are used, the anti-PKCg antibody most preferably includes a fluorescent tag or label for rapid detection using methods well known in the art. In preferred antibody-based methods, after the blood sample is contacted with the anti-PKCg antibody, the solution is passed over a column such as, for instance, a DEAE/ Sepharose column in order to separate the binding complexes from cells and larger proteins in the sample. Most preferably, according to a preferred method, the inbound (free) labeled anti-PKCg antibody will bind to the column, and the anti-PKCg antibody/PKCg complexes will flow through. Elimination of unbound labeled antibody from the sample improves the quantitative aspects of the method, making it possible to gauge progress or degree of ischemic insult to CNS tissues. The column may be washed one or more times to remove any of the larger complexes that may have bound. After collection of the flowthrough solution, the presence of any anti-PKCg antibody/PKCg complexes may be detected using methods well known in the art for detection of such complexes.

In another embodiment, the present invention provides a method for determining whether or not damage has occurred to the central nervous system as a result of a stroke or other event such as a transient ischemic attack, head trauma, myocardial infarction or other event resulting in disruption of cranial blood flow through the use of a sandwich antibody assay. According to the present invention, a first anti-PKCg antibody, raised against a specific epitope on the PKCg protein, is immobilized on a solid substrate. Preferably the solid substrate is a magnetic bead or alternatively the solid substrate may be a well of a microtiter plate. A sample of venous blood, drawn from an individual suspected of having a stroke or other event involving damage to the central nervous system, is contacted with the first antibody immobilized on the solid substrate to form an antibody/PKCg binding complex. A subsequent wash step may be employed to remove any unbound PKCg protein from the rest of the sample mixture. A second anti-PKCg antibody specific for a different PKCg epitope than the first antibody and being detectably labeled, e.g., with a fluoresceinated tag, is then contacted with the PKCg protein bound to the first antibody immobilized on the solid substrate under conditions suitable to form a binding complex with PKCg. A washing step may be included subsequent to this second binding step to remove any unbound labeled anti-PKCg antibody. Detection and quantitation of PKCg in the original sample may be conducted by methods well known in the art such as, for instance, a confocal microscope or calorimetric assay.

DEFINITIONS

As used herein, the term "ischemic event" refers to any potentially harmful episode resulting from temporary or permanent decrease or elimination of blood flow to tissues, particularly, with respect to the present invention, any event or physiological occurrence that interrupts blood flow to the CNS, especially cranial blood flow, and leads, without treatment, to damage in the central nervous system. Specific types of ischemic events include stroke, transient ischemic attacks, head trauma, myocardial infarction or other events resulting in interrupted blood flow to the CNS. Events resulting in such interrupted blood flow may be naturally occurring or unexpected (i.e., as in the case of stroke or accidental trauma) or may be the result of interventionary procedures, such as surgical procedures, surgical or physical mishaps, anesthesia, and therapeutic and pharmaceutical interventions, causing (undesired) interruption of blood flow, as a side effect.

DETAILED DESCRIPTION OF THE PREFERRED EMBODIMENTS

Figure 1:
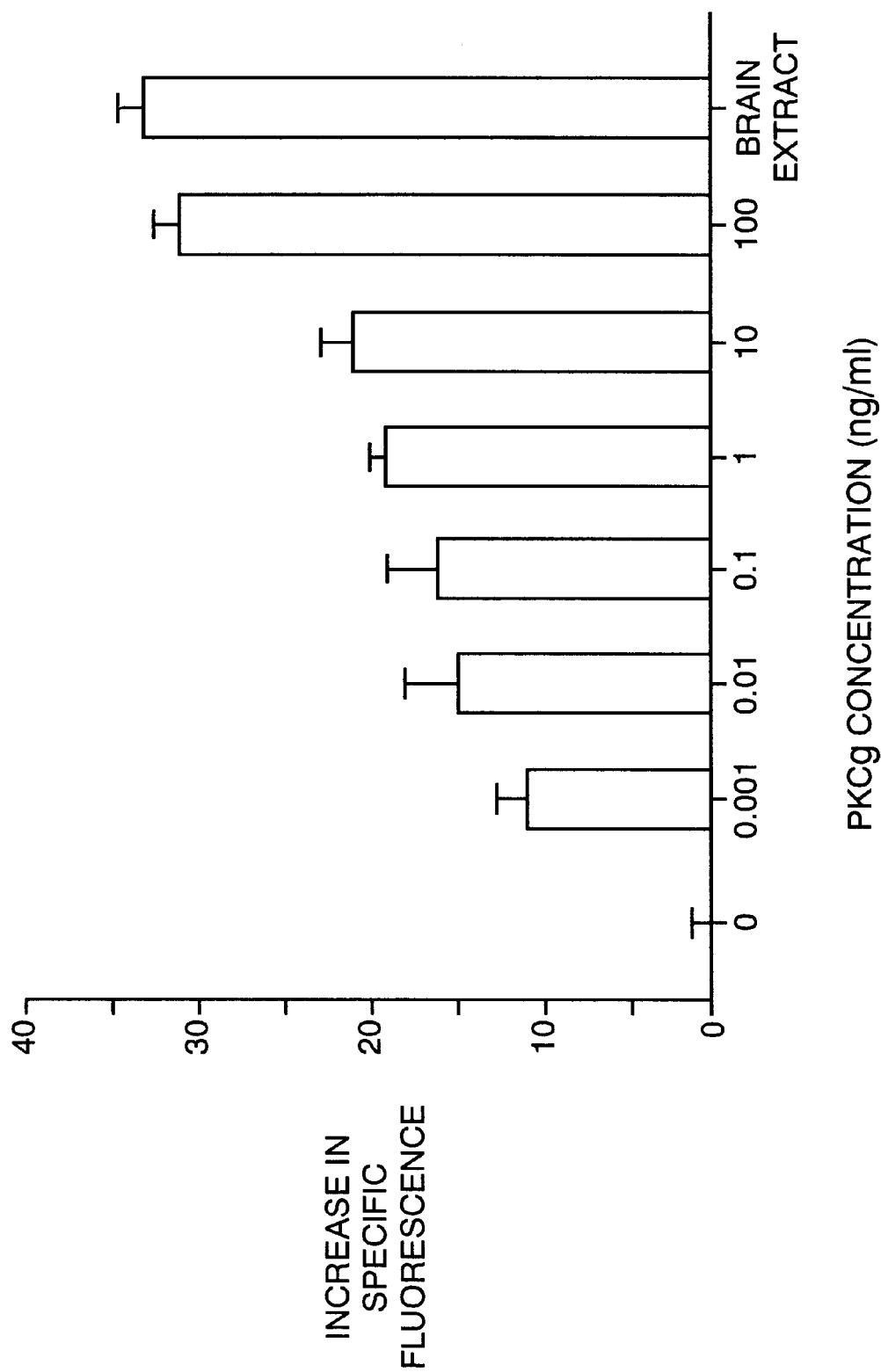
FIG. 1 shows PKCg dose-dependent percent fluorescence increase, from a sandwich-type immunosorbent assay measuring PKCg captured on anti-PCKg beads, detected with anti-PKCg-FITC.

The present invention describes a rapid and accurate method for detecting damage to the central nervous system caused by an ischemic event, which may result from stroke, transient ischemic attacks, head trauma, myocardial infarction or other events resulting in interrupted cranial blood flow. Traumatic events, such as stroke, cause a series of biochemical events as cell damage progresses. One of these biochemical events is the production of the gamma isozyme of protein kinase C(PKCγ or PKCg), which is expressed in the central nervous system as a result of an ischemic event.

PKCg is a specific marker for central nervous system tissue that is activated by certain fatty acid moieties such as arachidonic acid (AA). In addition, AA is the fully competent precursor of the oxygenase pathways. In the CNS, noteworthy pathways are cyclooxygenase, producing prostaglandins, thromboxanes and prostacyclins, and lipoxygenases (including 5-HETE, 12-HETE, $LTC_4$, LxA), which are also activated during ischemia and CNS injury. PKCg has been shown to be activated during and immediately following ischemia and traumatic CNS injury. PKCg is specific for the central nervous system is not normally found in peripheral blood. The discovery of the present invention follows the observation that the the blood brain barrier is often compromised as a result of an ischemic event, leading to appearance of PKCg in peripheral blood. It has further been discovered that the presence of PKCg in peripheral blood occurs and can be detected in peripheral blood almost immediately following an ischemic event, and, most importantly, within the critical time window in which diagnosis and treatment of ischemic injury can prevent permanent damage to CNS tissue.

Accordingly, the detection of PKCg in a peripheral blood sample is an early diagnostic indicator of an ischemic event such as stroke, TIA, head trauma or myocardial infarction, making early and effective treatment possible. Moreover, the amount of PKCg detected in a sample is proportional to the degree of the damage or insult to normal tissues, and therefore quantitative assay of the PKCg in a sample also is indicative of the extent of the trauma to the CNS.

Insult to brain tissue from stroke, transient ischemic attacks (TIAs), head trauma, myocardial infarction or other events resulting in the disruption of cranial blood flow share a common pathway of cell mediated damage which originates with the activation and eventual release of PKCg from neural tissues. PKCg is normally found only in the CNS and is not known to be localized to any other tissues. In the event of ischemic damage, there is an accompanying breakdown of the blood brain barrier, which results in the release of PKCg from its normal location in the brain into venous blood.

The methods of the present invention are especially contemplated to benefit human subjects, but they are of course suitable for any mammalian subject in which the presence of a PKCg isoform signals CNS damage.

Any means of detection for the PKCg marker is suitable, and any known means of detecting a specific protein in a sample may be employed. Preferably, PKCg is detected in a sample of blood from a mammalian subject, by contacting the sample with a binding partner for PKCg, that is, a peptide, immunoglobulin, small molecule or other moiety capable of forming an association complex with PKCg. Most preferably, the PKCg in a sample is detected using antibodies specific for PKCg. Several such antibodies are known, and monoclonal antibodies recognizing different epitopes of PKCg are available commercially, making simple sandwich assays readily practicable. (See Examples, infra.)

For detection or measurement of PKCg levels in a sample, fluorescently labeled antibodies are most preferred. Many other means of detecting PKCg directly or detecting a complex of PKCg with another moiety are known, including gas chromatography mass spectroscopy, thin layer chromatography, hydroxyl apatite chromatography, high pressure liquid chromatography, colloidal gold immunolabeling read by electron microscopy, enzyme-linked immunosorbent assays, radioactively labeled tags or antibodies specific for PKCg read using a scintillation counter, bioluminescently labeled antibodies read on a colorimeter, etc.; however, most of these methods require several hours or even days for sample preparation and/or measurement of the signal, making them inferior to sensitive fluorescence-based assays such as described in the examples (infra). Also, the apparatus necessary for detection in some cases (e.g., mass spectrophotometer, electron microscope) would not fit inside an ambulance, making performance of the assays by emergency medical personnel before the patient suspected of suffering an ischemic event is brought to a hospital impossible.

The materials necessary for detection of PKCg in a sample of venous blood are conveniently assembled into a kit, so that personnel treating or transporting a trauma victim can determine quickly whether an ischemic event has been suffered by their patient. One kit useful for such diagnoses is based on PKCg binding and is capable of providing multiple levels of detection and quantitation. The level of detection provides quantitative assessment of ischemic damage based on calibration of fluorescently tagged antibodies to PKCg detected in venous blood.

In addition to providing rapid diagnosis of an ischemic event by emergency and medical personnel, the methods and kits described herein also may be used to monitor PKCg levels as part of a routine checkup procedure or to monitor recovery from ischemic injury to CNS tissues. The nature of the methods and kits described herein make it possible to perform diagnosis and monitoring of ischemic events in many environments, for instance ambulances or other mobile medical facilities, laboratories, hospitals, emergency rooms, or even homes, sanitoria or other private facilities.

Examples illustrating the detection of PKCg as a means of detecting an ischemic event in accordance with this invention will be set forth below. The specific materials and parameters included in the following examples are intended to illustrate the practice of the invention, and they are not presented to in any way limit the scope of the invention.

EXAMPLE 1

The animal model of middle cerebral artery occlusion used in this example relies on an intraluminal filament technique in the rat (see, Zhao et al., 1994a,b). Rats were anesthetized with halothane in a nitrous oxide/oxygen mixture and the carotid artery exposed. A chamfered monofilament suture (3/0) was introduced into the ligated carotid artery, past the bifurcations of the external and common carotid, and the internal carotid and the pterygopalatine artery, into the intracranial circulation, where it lodged in the narrow proximal anterior carotid occluding the middle cerebral artery. The wound was then sutured and the animal allowed to recover from anesthesia. After 90 minutes of occlusion, neurologic function was assessed. The animal was then decapitated and trunk blood collected into a container containing 1.5 mg/ml EDTA which was frozen until analysis.

Blood samples were collected from three groups of animals: (1) untreated controls (n=3); (2) sham operated controls (n=3); and (3) ischemic animals (n=5). Neurologic function was assessed and graded from normal to severe impairment. The assessment scale is set forth in Table 1.

TABLE 1

Neurological Impairment in Control and Induced Mice

| Neurological Imairment Assessment | Severity | Score |
|---|---|---|
| No observable deficit | normal | 0 |
| Forelimb flexion; grip reflex present in both forepaws | moderate | 1 |
| Forelimb flexion; grip reflex present in contralateral forepaw only | severe | 1.5 |
| Forelimb flexion; grip reflex absent in both forepaws | severe | 2 |
| Forlimb flexion; grip reflex absent in both forepaws, plus circling toward paretic side | severe | 3 |

The neurological impairment scores of the control groups were 0 in both cases; the average impairment score of the ischemic group was 1.9.

These results demonstrate that the middle cerebral artery occlusion (MCA-O) procedure resulted in severe neurological damage, whereas neither the untreated nor sham operated control groups showed any signs of neurological damage. It was then demonstrated that the neurological impairment scores positively correlated with the amount of PKCg measured from peripheral blood samples of ischemic animals but not with sham operated or untreated control animals.

The assay of PKCg in samples of venous blood used an immobilized "capture" antibody specific for one epitope on the PKCg protein and a second "quantifying" antibody, which included a fluorescent marker attached thereto and which recognized a different epitope of PKCg than the capture antibody.

In the present example, the capture antibody was a polyclonal rabbit antiserum (Calbiochem; Catalog No. 539529, used at 1:500 dilution) recognizing the amino acid sequence extending from amino acids 306–318 of the PKCg protein. The quantifying antibody was a monoclonal antibody (Transduction Laboratories; Catalog No. P20420, used at 1:200 dilution) reactive with amino acids 499–697 at the carboxyl end of the PKCg protein. The quantifying antibody was fluoresceinated using a FluoroTag kit (Sigma Chemical). A brain extract sample was used as a brain-derived PKCg positive control 20 (Transduction Laboratories; Catalog No. B30900).

The capture antibody was immobilized on tosyl-activated magnetic Dynabeads (Dynal Catalog No. 142.03,1402.4). These materials allowed ease of imaging and quantification of the fluorescence using a confocal scanning laser microscope (Nikon PCM200 equipped with Fluorescein filters).

Paramagnetic beads coated with capture antibody and contained in a small test tube were placed in a holder containing a magnet, which attracted and pelleted the beads. Binding of the capture antibody to the magnetic beads was tested, after rinsing the beads in buffer, by resuspending in goat anti-rabbit IgG-fluorescein antibody solution which binds selectively to rabbit antibodies. Bright flouorescence observed by laser microscope confirmed binding of the capture antibody to the magnetic beads.

Once the capture antibody binding to the magnetic beads was confirmed, a standard curve was generated using known concentrations of PKCg (obtained from Calbiochem; Catalog No. 539627): 0 pg/ml, 1 pg/ml, 10 pg/ml, 100 pg/ml, 1 ng/ml, 10 ng/ml, 100 ng/ml, and brain extract. The various concentrations of PKCg were incubated with the beads and complexed with the capture antibody, then the quantifying antibody with the fluoresceinated label was added and complexed fluorescence measured using intensity-measuring software on the confocal microscope. Fluorescent intensity measurements from 3 separate bead preparations are shown in FIG. 1. Measurement bias was minimized or eliminated by writing a macro for the measurement software, whereby a fixed-diameter circle was used to delineate an area for intensity measurement in at least 200 beads per concentration. Only beads that were in focus within the image plane were measured for fluorescence intensity. As seen in FIG. 1, the fluorescensce intensity, taken as a mean of >100 beads per dose of PKCg, increases in a dose-dependent fashion. The data in FIG. 1 are expressed as % increases in specific fluorescence, which were derived from subtracting the baseline fluorescence from the increase in fluorescence due to anti-PKCg-FITC antibody binding to the PKCg.

Figure 2:
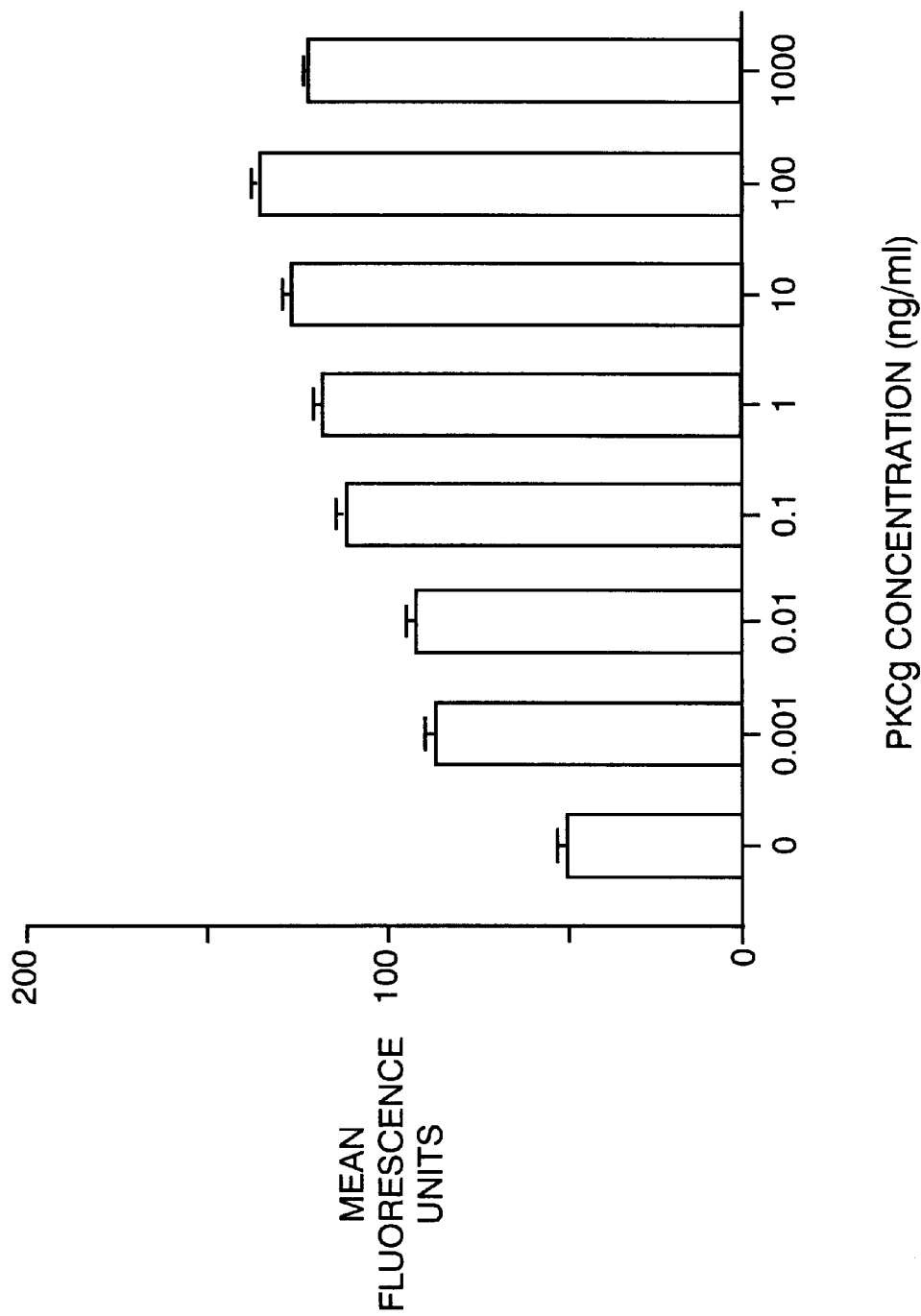
FIG. 2 shows PKCg dose-dependent fluorescence in mean fluorescence units, from a sandwich-type immunosorbent assay measuring PKCg captured on anti-PCKg coated beads, detected with anti-PKCg-FITC.
Figure 3:
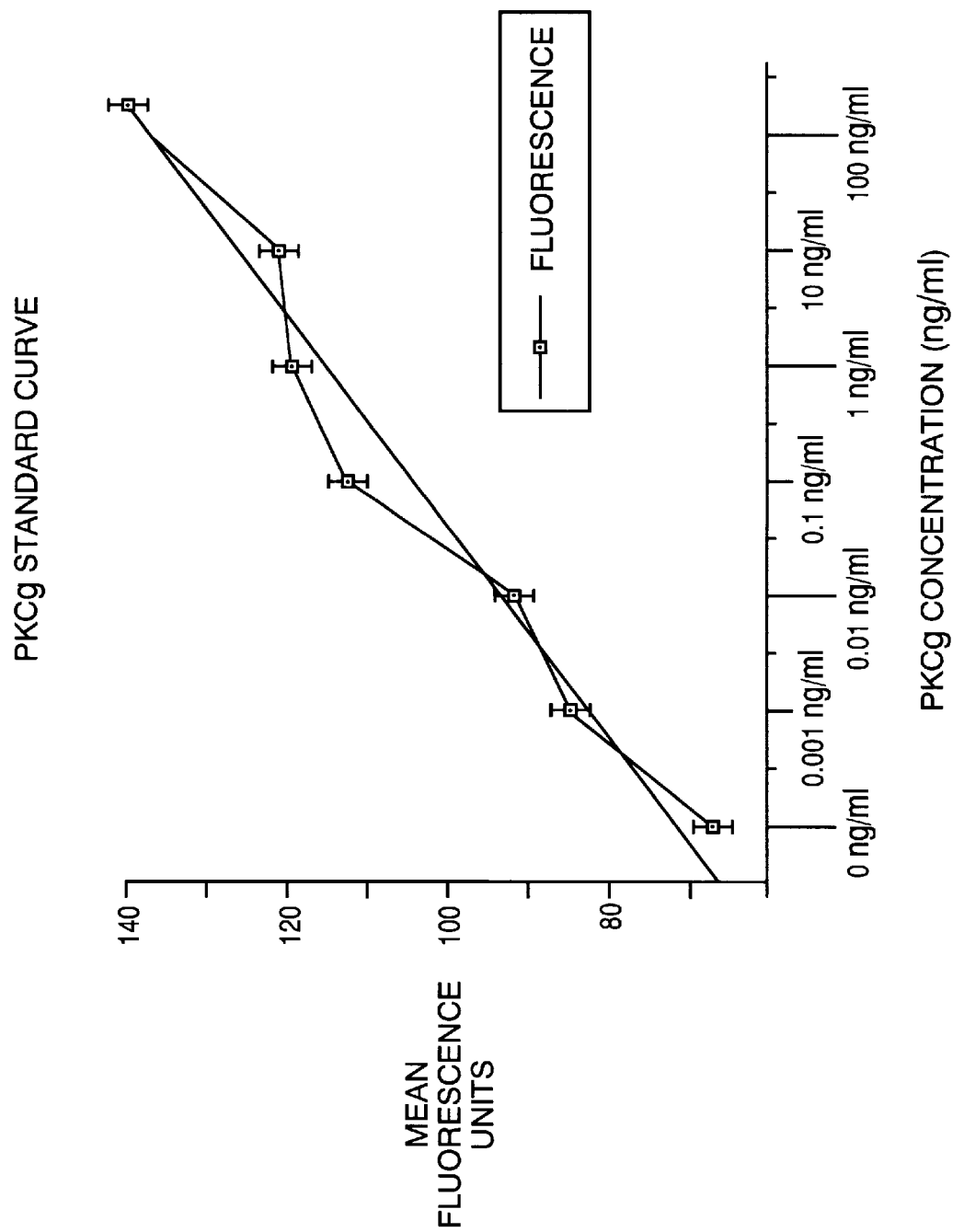
FIG. 3 shows a PKCg standard curve generated from the data depicted in FIG. 2.

In order to establish a standard curve from the dose response curves derived from increasing concentrations of PKCg, the fluorescence intensity was again measured from beads using the confocal microscope, however the fluorescence intensity measurements were left as fluorescence units, as seen in FIG. 2. A simple curve fit was used to establish the standard curve of fluorescence intensity due to increasing concentrations of PKCg. The standard curve is shown in FIG. 3. The standard curve of PKCg-induced fluorescence was used to establish the levels of PKCg found in trunk blood of surgically treated rats. The PKCg concentrations were read directly from the standard curve.

Figure 4:
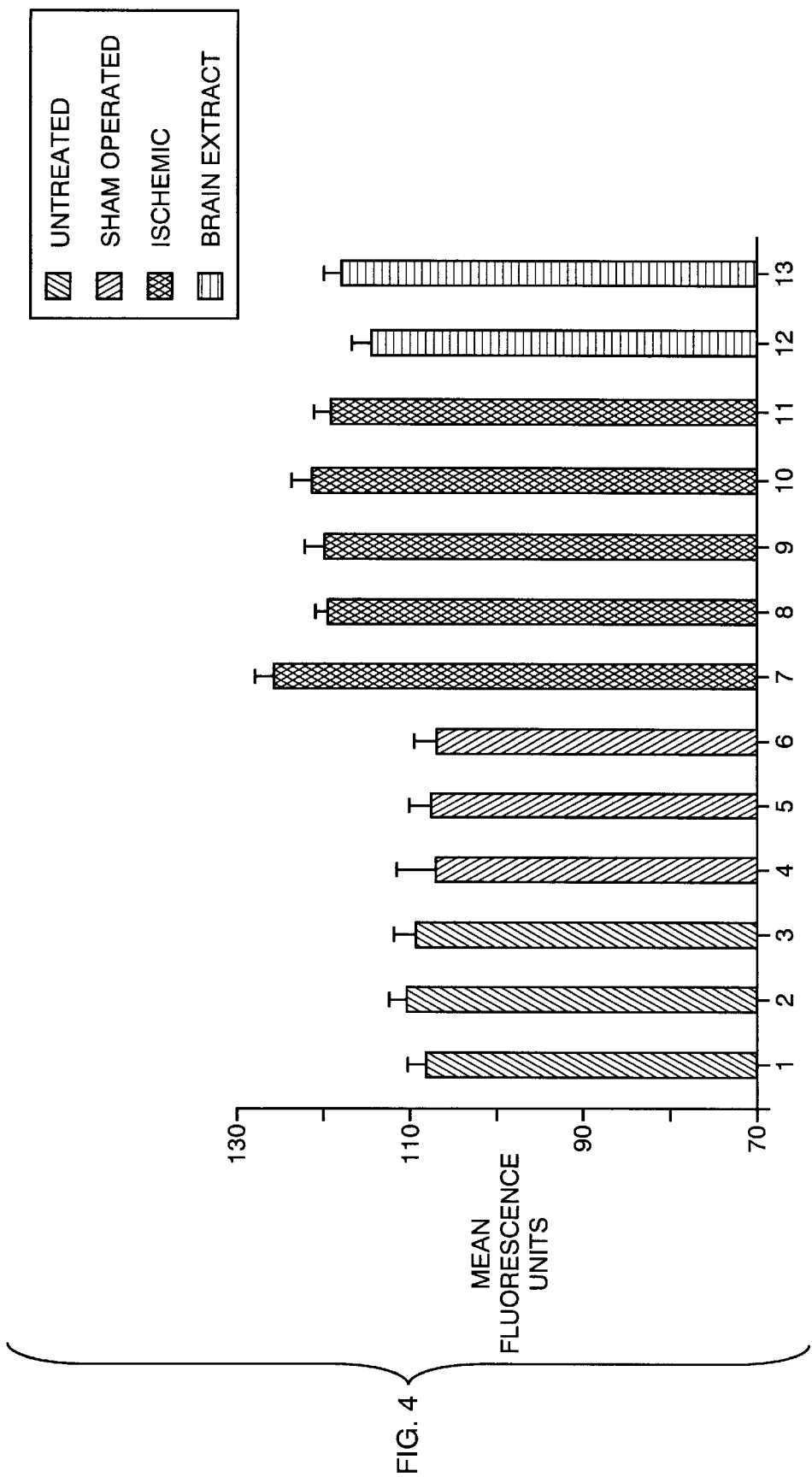
FIG. 4 shows differences in detected level of PKCg in untreated (#1–#3), sham treated (#4–#6), and ischemic (#7–#11) subjects from tested peripheral blood samples. Levels of PKCg in brain extract are also shown (#12, #13).

Results from the blood samples demonstrate that the sandwich technique is sensitive enough to detect significant increases in the PKCg in peripheral blood samples following the MCA-O procedure. (See FIG. 4). As seen in FIG. 6, blood from the untreated and sham operated control animals showed significantly less fluorescence in every case when compared to the ischemic animals. In addition, brain extract controls also show significantly higher fluorescence levels than the untreated and sham controls.

Figure 5:
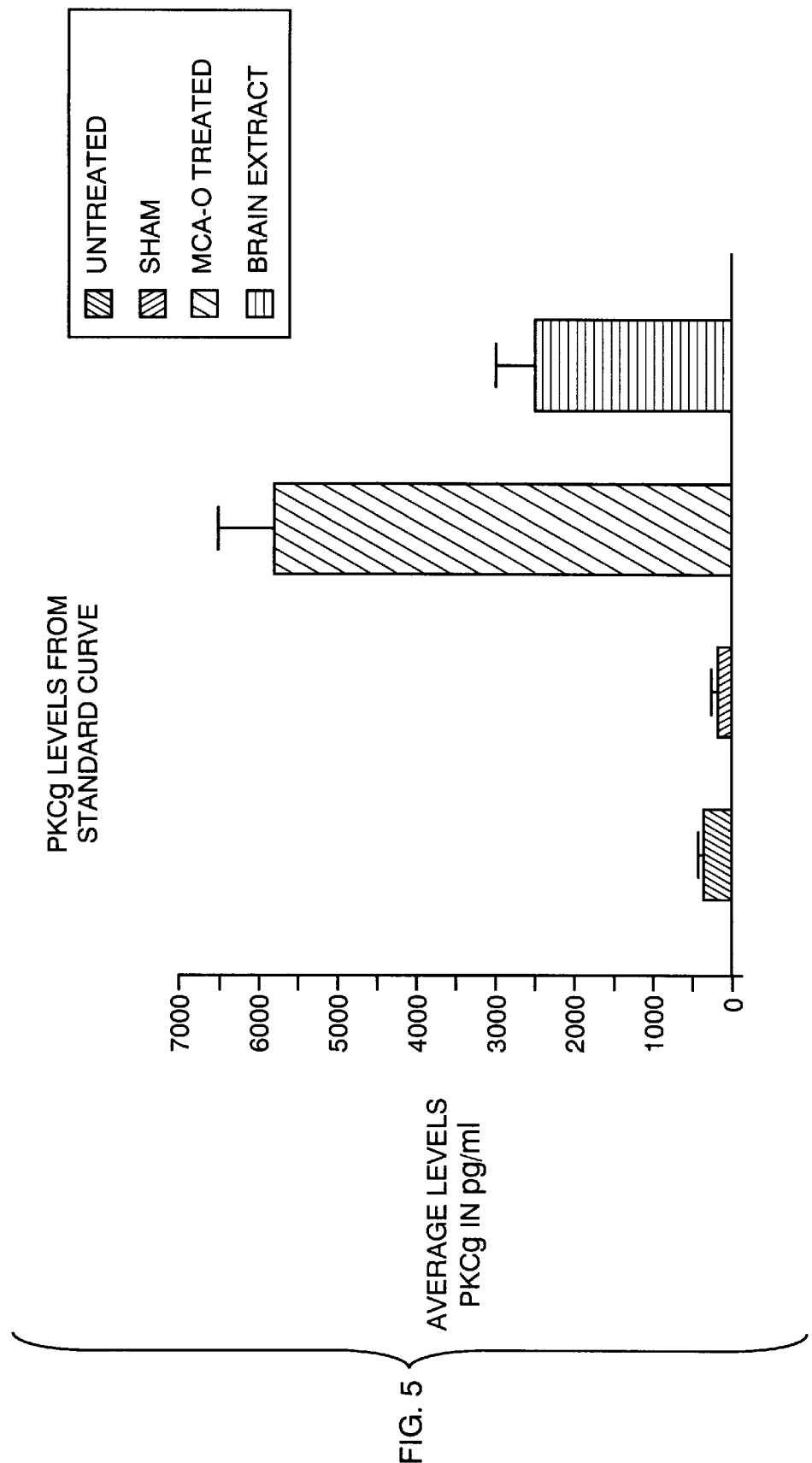
FIG. 5 shows differences in PKCg levels among untreated, sham operated, and ischemic subjects detected in peripheral blood, and in brain extract, where PKCg amounts are read from the standard curve (see FIG. 3).

When fluorescence levels are converted to picograms of PKCg per ml using the standard curve shown in FIG. 3, the difference in surgical treatments on PKCg levels becomes even more pronounced, as illustrated in FIG. 5. FIG. 5 shows a dramatic increase in the detectable levels of PKCg following the ischemic event. Levels of PKCg detected in blood collected outside of the brain following MCA-O are more than 50% higher than levels of PKCg derived from brain extract.

PKCg is activated and mobilized at the time of the ischemic event. PKCg is released from damaged cells where it initiates several damage cascades including the arachidonic acid and lipoxygenase cycles. PKCg also initiates glutamate-induced excitoxicity cascades. One of the events which rapidly follows the ischemic episode is at least a transient breakdown of the blood-brain barrier. At 90 minutes following the MCA-O procedure, the trunk blood samples contained levels of PKCg that are approaching 6 ng/ml as determined from the antibody sandwich technique using the magnetic beads.

This ischemic level is at least ten times the limit of PKCg detection (600–1000 pg/ml) that has been shown using this method. This is an acceptable ratio of detection to actual measurements, which confirms the utility of the sandwich assay format to monitor ischemic events measured from a peripheral blood sample. The PKCg detection can also be performed visually from confocal images of beads bound with a fluorescent quantifying antibody.

Experience with the sandwich-type assay described above has led to a preferred protocol for the assay of this invention:

Detection and Quantitation of PKCg in a Venous Blood Sample

1. Dilute capture antibody to 1:500 using a 0.1M Na-phosphate buffer (pH 7.4) containing 1% BSA (Fraction V, Sigma Chemical) and 0.1% Tween-20 detergent (Sigma Chemical). To make Na-Phosphate buffer use 2.62 g $NaH_2PO_4$ (MW=137.99) and 14.42 grams $Na_2HPO4.2H_2O$)(MW=177.99) in 1 liter distilled water and adjusted pH to 7.4. Add capture antibody to plastic 96-well microtiter plate (or other vessel) and incubate at 37° C. for at least 2 hr.
2. Rinse plate with the PBS/Tween/BSA 2–3 times to remove unbound antibody from plate wells. Minimal changes to this procedure will not effect antibody binding.
3. To prevent non-specific binding, block wells with 200 $\mu$l of 10% fetal calf serum in PBS for at least 2 hr. It is possible to substitute 10% horse serum or 3% BSA (Fraction V, Sigma Chemical). Rinse 2–3 times with the PBS/Tween/BSA solution mentioned above.
4. Add standards or samples to the well(s), dilute in PBS/ 10%serum (50–100 $\mu$l sample size) and let stand for 30 min.–1 hr. at 37° C. Wash 4 times using PBS/Tween/BSA.
5. Add quantifying antibody and incubate for 30 min. Wash 4 times using PBS/Tween/BSA.
6. Read fluorescence on a fluorimeter, such as a CytoFluor II from Perseptives Instruments. Fluorescein optics were used with an excitation of 450 nm, and emission at 515nm.

Although a number of embodiments have been described above, it will be understood by those skilled in the art that modifications and variations of the described compositions and methods may be made without departing from either the spirit of the invention or the scope of the appended claims. The publications cited herein are incorporated by reference.

REFERENCES

The following publications pertain to the state of the art and/or illustrate techniques that may be utilized in practicing the present invention.

Adams et al., Guidelines for the Management of Patients with Acute Ischemic Stroke, Stroke, 25(9): 1901–1914, September 1994.

Bazan, Effect of Ischemia and Electroconvulsive Shock on the Free Fatty Acid Pool in the Brain., *Biochim. Biophys. Acta*, 218: 1–10, 1970.

Buttner et al., S-100 Protein: Serum Marker of Focal Brain Damage After Ischemic Territorial MCA Infarction, Stroke, 28: 1961–1965, 1997.

*Conn's Current Therapy*, R. E. Rakel, ed., W. B. Saunders Co. (1993), pp. 840–851.

Dippel et al., We Need Stronger Predictors of Major Vascular Events in Patients With a Recent Transient Ischemic Attack or Nondisabling Stroke, Stroke, 28: 774–776, 1997.

Feinberg et al., Guidelines for the Management of Transient Ischemic Attacks, Stroke, 25(6): 1320–1335, June 1994.

Madden et al., Glutamate, Arachidonic Acid, and Calcium Regulation in Cultured Hippocampal Astrocytes: Involvement in Ischemia?, in *Cellular and Molecular Mechanisms of Ischemic Brain Damage. Advances in Neurology*, Siesjo and Wieloch, eds., Lippincott-Raven (Philadelphia 1996), 71: 53–60.

Missler et al., S-100 Protein and Neuron-Specific Enolase Concentrations in Blood as Indicators of Infarction Volume and Prognosis in Acute Ischemic Stroke, Stroke, 28: 1956–1960, 1997.

Shashoua et al., Proteins of the Brain Extracellular Fluid: Evidence for Release of S-100 Protein, *J. Neurochem.*, 42(6): 1536–1541, 1984.

Wieloch et al., Intracellular Signal Transduction in the Postischemic Brain. in *Cellular and Molecular Mechanisms in Ischemic Brain Damage. Advances in Neurology.*, Siesjo and Wieloch, eds., Lippincott-Raven (Philadelphia 1996), 71: 371–388.

Wolfe, Eicosanoids: Prostaglandins, Thromboxanes, Leukotrienes and Other Derivatives of Carbon-20 Unsaturated Fatty Acids, *J. Neurochem.*, 38: 1–14, 1982.

Zhao et al., Hyperthermia complicates middle cerebral artery occlusion induced by an intraluminal filament, *Brain Res.*, 649: 253–259, 1994a.

Zhao et al., Delayed treatment with the spin trap alpha-phenyl-N-tert-butyl nitrone (PBN) reduces infarct size following transient middle cerebral artery occlusion in rats, *Acta Physiol. Scand.*, 152: 349–350, 1994b.

What is claimed is:

1. A method for detecting an ischemic event associated with injury to the central nervous system in a mammalian subject comprising:
   (a) contacting a peripheral blood sample obtained from said subject with a detectably labeled binding partner capable of forming a binding complex with protein kinase C gamma (PKCg);
   (b) detecting the presence of a PKCg/binding partner complex formed in step (a), wherein detection of said PKCg/binding partner complex indicates that an ischemic event has occurred.

2. The method according to claim 1, wherein said binding partner is immobilized on a finely divided solid substrate dispersible in a fluid sample, which substrate exhibits a surface moiety capable of complexing PKCg.

3. The method according to claim 1, wherein said binding partner is in the form of an anti-PKCg antibody.

4. The method according to claim 3, wherein said anti-PKCg antibody is fluorescently labeled.

5. The method according to claim 1, wherein the ischemic event is the result of stroke, transient ischemic attack, head trauma, myocardial infarction or trauma resulting in interrupted cranial blood flow.

6. A method for detecting an ischemic event in a mammalian subject comprising the steps of:
   (a) contacting a peripheral blood sample obtained from said subject with a first anti-PKCg antibody immobilized on a solid substrate under conditions suitable for forming a binding complex with PKCg in said sample;
   (b) contacting the substrate with a second antibody comprising a detectably labeled anti-PKCg antibody under conditions suitable for the second antibody to react with PKCg, wherein said second antibody recognizes a different PKCg epitope than said first antibody;
   (c) measuring the presence of the detectable label to detect PKCg in said binding complex, wherein detection of PKCg in said complex indicates that an ischemic event has occurred.

7. The method according to claim 6, which further comprises the step, after step (a):
   a-1) separating the solid substrate from the rest of said sample.

8. The method according to claim 7, which further comprises the step, after step (b):
   b-1) removing any unbound second antibody.

9. The method according to claim 8, which further comprises the step of quantitating the level of PKCg in the blood sample based on the amount or intensity of the detectable label measured in step (c).

10. The method according to claim 6, wherein the substrate is a microtiter well.

11. The method according to claim 6, wherein the substrate is a magnetic bead.

12. The method according to claim 6, wherein the second antibody is fluorescently labeled.

13. The method according to claim 6, wherein the ischemic event is the result of stroke, transient ischemic attack, head trauma, myocardial infarction or trauma resulting in interrupted cranial blood flow.

14. A method for diagnosing an ischemic event associated with injury to the central nervous system, wherein said ischemic event is selected from the group consisting of stroke, transient ischemic attack, head trauma, myocardial infarction, and trauma resulting in interrupted cranial blood flow in a mammalian subject comprising:
   contacting a peripheral blood sample obtained from said subject with a binding partner capable of forming a binding complex with PKCg;
   detecting the presence of a PKCg/PKCg binding partner complex in the subject's peripheral blood, wherein detection of a PKCg/PKCg binding partner complex indicates that said ischemic event has occurred.

15. The method according to claim 14, wherein the PKCg binding partner is detectably labeled.

16. The method according to claim 15, wherein the detectably labeled PKCg binding partner is a detectably labeled anti-PKCg antibody.

17. A kit for rapid diagnosis of injury resulting from an ischemic event in a mammalian subject, comprising:
   a) a solid substrate having immobilized thereon a first anti-PKCg antibody,
   b) a second anti-PKCg antibody reactive with a different epitope of PKCg than is recognized by said first anti-PKCg antibody, which second anti-PKCg antibody is detectably labeled, and
   c) instructions and reagents for performing a sandwich-type assay for the presence of PKCg in a sample of peripheral blood obtained from said subject.

18. A kit according to claim 17, wherein said first antibody is immobilized on magnetic beads.

19. A kit according to claim 17, wherein said first antibody is immobilized in wells of a multi-well microtiter plate.

20. A kit according to claim 17, wherein said second antibody is fluorescently labeled.

* * * * *